United States Patent [19]

Lynch

[11] 4,417,876
[45] Nov. 29, 1983

[54] NONDESTRUCTIVE DENTAL CAP REMOVAL METHODS

[76] Inventor: Joseph A. Lynch, 51 E. 1st Ave., Hialeah, Fla. 33010

[21] Appl. No.: 329,735

[22] Filed: Dec. 11, 1981

[51] Int. Cl.³ .............................................. A61C 3/00
[52] U.S. Cl. .................................................. 433/161
[58] Field of Search ........................ 433/161, 158, 154

[56] References Cited

U.S. PATENT DOCUMENTS 3,579,834  5/1971  Reed ..................................... 433/154
3,889,376  6/1975  Zatkin ................................... 433/161
4,187,610  2/1980  Ziegler .................................. 433/24

Primary Examiner—Robert Peshock
Attorney, Agent, or Firm—Laurence R. Brown

[57] ABSTRACT

Dental bridge or crown caps are removed by drilling a hole in the crown for inserting the end of a bolt to contact the tooth stub. The bolt is in a metal stabilizing bar member which rests in balanced and aligned position upon the cap structure and is connected thereto as a unit that moves together by means of wire or equivalent flexible means wrapped thereabout and tightened so that the bolt pressure on the tooth stub will apically lift the crown without shear stresses.

10 Claims, 12 Drawing Figures

NONDESTRUCTIVE DENTAL CAP REMOVAL METHODS

TECHNICAL FIELD

This invention relates to the removal of dental crown and bridge caps anchored on shaped tooth stubs and more particularly it relates to the binding together of a dental cap in situ with a stabilizing tool assembly adapted to contact the tooth stub with a dislodging pressure for unseating the cap.

BACKGROUND ART

In the dental arts tooth crown and bridge caps are cemented securely and firmly onto one or more shaped stubs for support. On some occasions it becomes necessary to remove the caps for dental work, such as, if caries develop under the caps or if the cap becomes partly loosened. In the prior art it has been very difficult to remove caps non-destructively. If caps are ceramic they are readily fractured. If they involve even more expensive bridges, they can be broken or twisted requiring significant rework.

Typical prior art tools and methods for dental cap removal include the following U.S. patents:

S. R. Sykes U.S. Pat. No. 2,428,689 Oct. 7, 1947
D. J. Wilson U.S. Pat. No. 3,755,901 Sept. 4, 1973
J. A. West U.S. Pat. No. 1,109,096 Sept. 1, 1914
G. J. Lozano et al. U.S. Pat. No. 3,690,006 Sept. 12, 1972
C. C. Reed Jr. U.S. Pat. No. 3,579,834 May 25, 1971

All of these patents involve clamps for engaging and holding the caps in order to pull them off. These clamps however have a tendancy to slip off, to fracture ceramic caps or to bend, strain and twist bridgework. Furthermore, there is considerable shear force exerted on the cap and/or tooth stub by many of these prior art tools and methods that tend to damage the caps and or tooth stubs and cause patient pain and discomfort in the removal process. Also some of the tools are either so delicate because of limited space that they are not strong or they conversely take up so much room that they cannot be used in the limited work space available in the mouth.

An undercutting method and tool in G. W. Anderson U.S. Pat. No. 4,179,816 Dec. 25, 1979 has been proposed for insertion under a crown to force the crown off by pressure on small thin cap surface area. This method and tool cannot be used with permanently cemented caps having high adhering forces without rupturing the cap without removal. Also this method is not feasible for use to remove bridgework.

Similarly the custom made gripping jaw surface of A. M. Zatkin U.S. Pat. No. 3,889,376 June 17, 1975 is strictly for crowns and takes up so much room that it is difficult to use in the limited space available. It is also only feasible for symmetrical type crown usage without providing significant shear forces that tend to fracture the crown and cause tooth stub damage and patient discomfort. Limited contact is made with the crown on diametrically opposed sides which cause problems of balance, grasping area and limitation to crown shape.

Thus, this invention proposes to improve the state of the art by curing the defects of prior art cap removal methods and tools including those above identified. There is provided simple, universal means and methods of removing both crown and bridge cap structure without significant shear forces compatible with very limited work space in a mouth and the various configurations of caps that might be encountered.

Other features, advantages and structural distinctions will be made apparent throughout the following description, drawings and claims.

DISCLOSURE OF THE INVENTION

This invention provides nondestructive means and methods of removing dental crown and bridge caps anchored on at least one shaped tooth stub. Thus a metal stabilizing member with a bolt threaded therethrough is positioned with the bolt apically aligned with the tooth stub through an access hole in the cap to the tooth stub to provide a force for pulling off the cap without substantial shear forces on the cap or tooth stub. The stabilizing member is preferably balanced in stable position with an intermediate layer of quick cure plastic deposited on one or more teeth and or cap elements holding the stabilizing member in place in aligned stable position. Laterally extending projections on the stabilizing member, which is generally in the form of a metal bar, enhance the hold of the plastic and the stability and balance of the member.

The cap and stabilizing member are then secured together as a composite unit for common movement together by wraps of flexible filamentary means, preferably wire, nylon or equivalent braided strands, tightly secured about the cap and stabilizing member.

Dislodging pressure on the cap is then apically applied by rotation of the threaded bolt against the tooth stub to move the composite unit, namely the cap and the metal stabilizing member, away from the tooth stub.

The wire or filamentary wrap is secured tightly about the cap and stabilizing member by means of a sleeve placed about two strands, generally the ends of the filamentary means. The sleeve is moved to tighten the wrap and then crimped in place to hold the wrap tightly secure in place. Crimping tools are also provided for this purpose.

For special usage with crowns a grooved plate is placed on one side of the crown to frictionally contact the crown on one side and to receive the filamentary means in the grooves on the other side. The wrap is then passed circumferentially about the entire crown.

PREFERRED EMBODIMENTS

Figure 1:
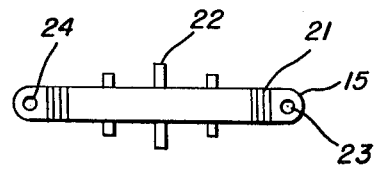
FIGS. 1 and 2 are respectively top and side view sketches of a metallic stabilizing member used in accordance with this invention for removal of dental bridgework caps from tooth stubs upon which the bridgework is cemented.
Figure 2:
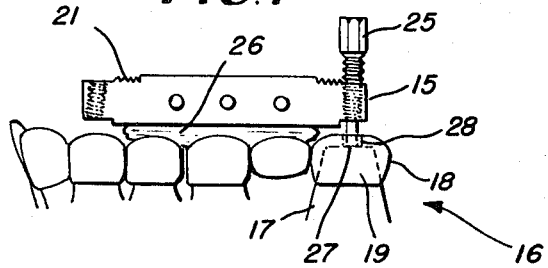

In FIGS. 1 and 2 a metal stabilizing bar member 15 is adapted to rest upon a row of teeth 16, one 17 of which has a removable cap 18 which is in the form of a crown or is part of a bridge assembly. The cap 18 is anchored on the shaped stub 19 of the tooth 17 by cementing and thus must be forcefully removed, if necessary. The stabilizing bar member 15 has ridges 21 for receiving and mating wire or similar filamentary loops thereinto and is supplied with lateral projections 22 which may be pins driven into holes or integrally formed fingers. A pair of threaded holes 23, 24 receive a threaded bolt member 25 respectively in vertical or slanted direction.

Thus as seen in FIG. 2 the stabilizing bar member 15 may be disposed upon the row of teeth 16 and positioned on the intermediate layer of fast setting cement 26 for stabilization in a fixed position to extend the end 27 of the bolt member 25 through a hole 28 in the crown 18 thereby to contact and press against the tooth stub 19 in a direction apically aligned to avoid shear stresses. The slanted hole 24 and angled stabilizing member 15 of FIG. 4 give flexibility for various in situ locations in a mouth for removing caps in lower and upper teeth locations, etc.

Figure 3:
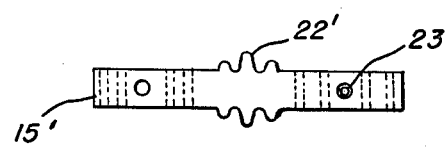
FIGS. 3 and 4 are similar views of an alternative embodiment illustrating the cap removal procedure.
Figure 4:
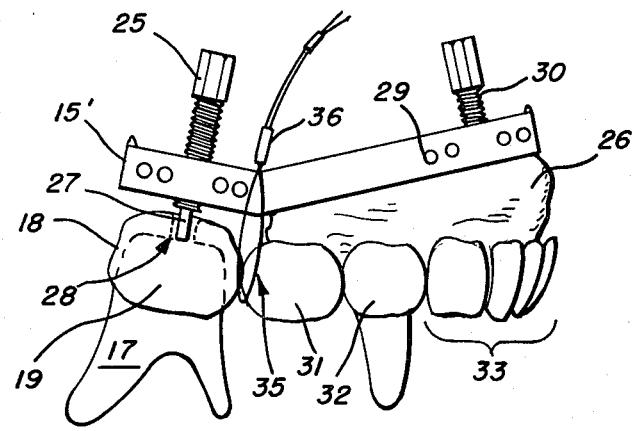

The modified stabilizing member 15' of FIGS. 3 and 4 provides integral fingers 22', lateral holes 29 and a bolt plug 30 to prevent cement 26 from entering threaded hole 23. The bridgework member cap of this embodiment comprises cap 18 and bridge members 31, 32. It is noted that cement layer 26 sticks to the stablizing member 15' by contact with fingers 22' etc., but not to the teeth 33 etc. Thus the bridgework cap and stablizing member 15' moves upwardly as a composite unit because it is held together by the flexible filamentary wire, etc. noose 35 tightened thereabout and held in place by the crimped sleeve 36.

Figure 7:
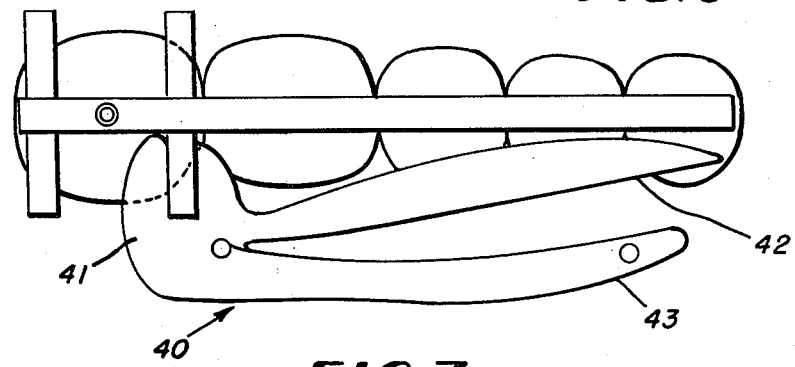
FIG. 7 is a diagrammatic view of a crimping tool afforded by the invention operable in situ on dental work, FIGS. 8A and B are respective top and buccal views of a crown cap and associated implement afforded by this invention.

The noose is secured about the bridgework cap and stabilizing member by wrapping the flexible wire or cord thereabout, tightening and securing in place. In accordance with this invention that can be done in situ in the close working space available in the mouth with simple tools including a crimper 40 shown in FIG. 7, which preferably has a 90° crimper head 41 extending from gripper handles 42, 43.

Figure 5:
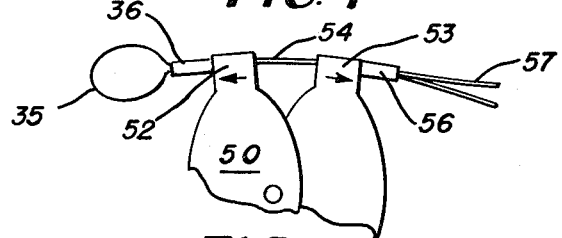
FIGS. 5 and 6 are respective plan and side view fragmental sketches of a dental tool used to tighten a wire or filamentary noose tightening tool afforded by this invention.
Figures 6, 9:
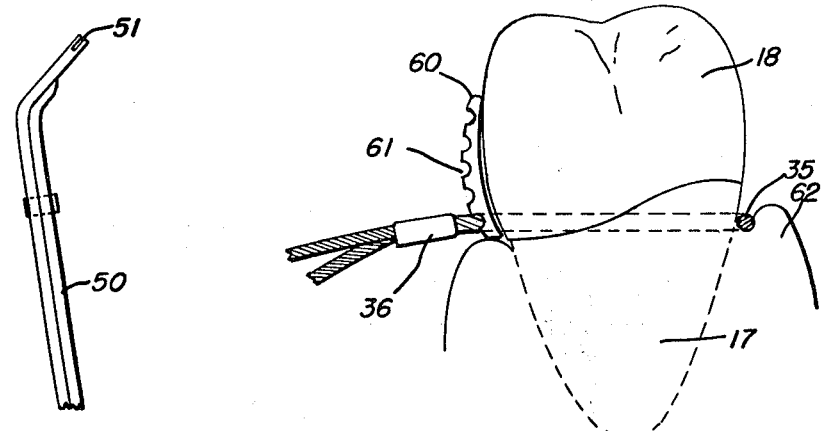
FIGS. 9 and 10 are fragmental side and top views respectively of a crown cap and filamentary noose used for removal of the cap as afforded by this invention.

The tightening is achieved with a tool 50 such as shown in FIGS. 5 and 6, preferably angled to enter the mouth as shown in FIG. 6. The grooves 51 on two separating jaws 52, 53 permit the flexible wire etc. strands 54 to enter but not the sleeves 36, 56. Thus if the sleeve 56 is crimped near the wire ends 57, then the sleeve 55 can be separated from anchor sleeve 56 by separating jaws 52, 53 to tighten the noose 35. When the noose 35 is appropriately tightened around the members then the sleeve 36 is crimped in place to lock the noose in its tightened position as shown in FIG. 4.

Thereafter it is seen that rotation of bolt 25 (FIG. 3) will apply pressure or force against the tooth stub 19 to force or lift the cap structure off the tooth 17 without shear forces which can bend or fracture the cap 18 or other parts of the bridgework. Thus, crowns and bridges may be non-destructively removed in accordance with this invention.

The access hole 28 need be drilled properly through the crown 18 to reach the tooth stub 19 against which the end of the bolt 27 rides. Stranded, nylon, steel, monel and hybrid flexible cords and wires can be used for appropriately giving adequate strength and workability. Other configurations of the stabilizing bar member can be employed and the tightening of the wire wrap can be done in other ways. It is however significant in accordance with this invention that the wire or equivalent cord flexible noose wrap is adaptable to many sizes and shapes of bridges and crowns and to in situ close working conditions in the mouth. Also it provides means for removal of bridges and crowns without damage so that they can be reinstalled without reconstruction or repair.

Figure 8:
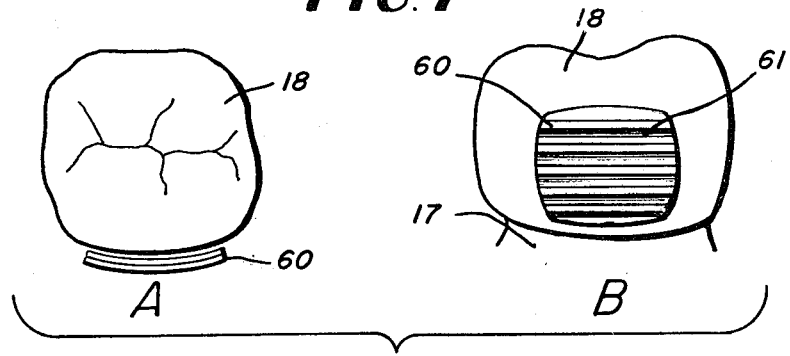
Figure 10:
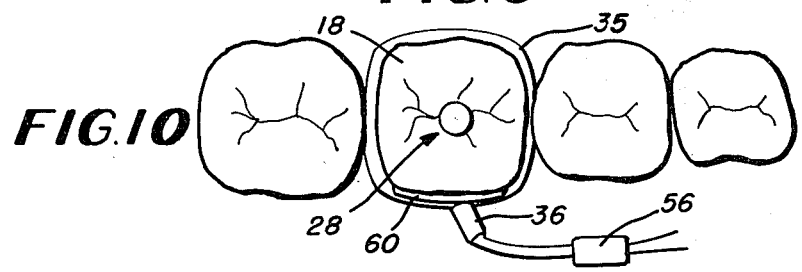
Figure 11:
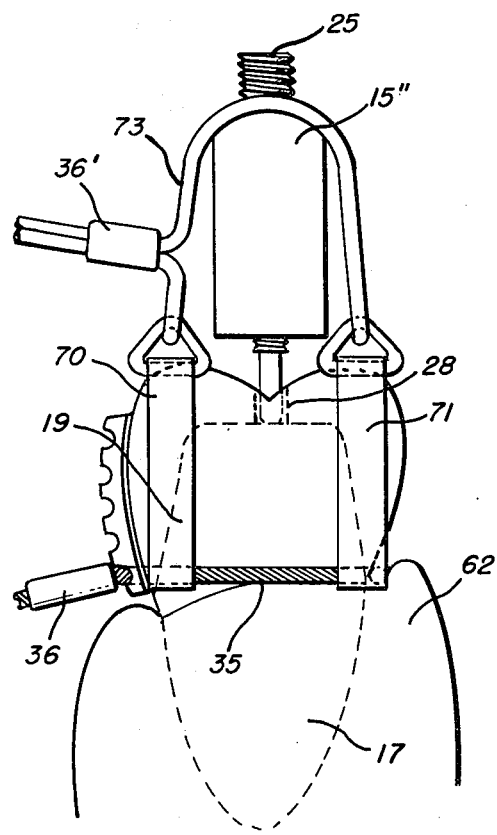
FIGS. 11 and 12 are two embodiments of the apparatus used in removing crown caps in accordance with this invention.
Figure 12:
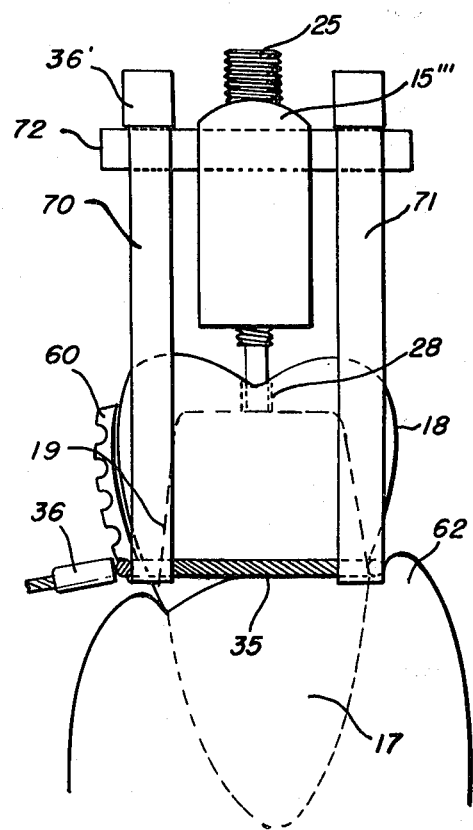

Conditions for grasping and removing a crown present even more problems that the bridges, but they also are removable by the techniques and tools of this invention as hereinbefore described. FIGS. 8 to 12 set forth the particular characteristics of crown removal. Thus, in FIG. 8A is a top view and in FIG. 8B a buccal view of a crown 18 on a tooth 17. It is noted that a grooved metal plate 60 is roughly shaped to rest on the buccal surface of the crown and provides a receptacle groove structure 61 for holding the filamentary means in the case of a crown first wrapped circumferentially about the crown as shown in FIGS. 9 to 12. The plate is preferably generally eliptical in shape and could be used on the labial crown surface as well. The inner surface of the plate is sand blasted with 60 micron particles of aluminum oxide and micro filled with a dental resin such as that sold by the trade name "Profile". This will as it is curing stick temporarily to the porcelain crown surface near the gingva and conform the inner shape to the porcelain crown shape. The place is then marked by a pencil, etc. and the plate is reset with cyano-acrylate instant glue. The grooves 61 are transverse and can contain therein, for example, a seven strand stainless steel wire noose and help prevent it from rising on the crown during tightening, lifting, etc. In general the larger upper circumference of the crown will contact with the grooved plate to prevent rising of the noose.

As shown in FIGS. 9 to 12 the noose 35 is tightened about the crown circumference at the gingva level as indicated by gum 62. It is seen from FIGS. 11 and 12 that the circumferential noose 35 grasps the crown and lifting is achieved by further flexible filamentary means comprising bands 70, 71 which are connected to the stabilizing member 15" or 15"' by means of an appropriate yoke such as cross bar 72 or a further filamentary coupling 73. Thus as before described the bolt 25 in stabilizing member 15", 15"' provides removal force through hole 28 in the crown by pressing on shaped tooth stub 19 to break loose and lift the crown from the stub 19 via the flexible filamentary means 35, 70, 71, 73.

Having therefore provided improved methods and implements for nondestructive removal of crown and bridge caps, those features of novelty believed descriptive of the nature and spirit of this invention are defined with particularity in the claims.

Industrial Use

This invention provides methods of non-destructively removing dental bridge and crown caps with a simple set of instruments comprising a metal stabilizing bar with threaded bolt therethrough with crimping and tightening tools for wrapping wire about the stabilizing bar and dentalwork.

I claim:

1. The improved non-destructive method of removing dental crown and bridge caps anchored on a least one shaped tooth stub, comprising the steps of, disposing a metal stabilizing member with a bolt threaded therethrough with the bolt extending through the hole in contact with the tooth stub in a substantially stabilized position for raising the cap without shear forces from the tooth stub by means of pressure on the stub when the bolt is pressed against the stub, securing flexible filamentary means about the cap and stabilizing member with the stabilizing member in said stabilized position to grasp the cap and form with the stabilizing member a composite unit that may be moved to dislodge the cap from the tooth stub, and producing a dislodging pressure for non-destructive unseating of the cap from the stub by rotation of the threaded bolt against the tooth stub to thereby move said composite unit away from said stub.

2. The method defined in claim 1 for removing a bridge including the step of stabilizing said stabilizing member on said bridge by introducing between the stabilizing member and the bridge a quick cure plastic buffer layer and letting it cure before securing the filamentary means.

3. The method defined in claim 1 including the steps of removing a bridge by providing on said stabilizing member a single extending bolt for contact with a single said tooth stub, and moving the stabilizing member and cap upwardly off said stub together in unison as a unit by means of said bolt.

4. The method of claim 1 wherein the securing comprises wrapping the filamentary means about the cap and stabilizing member with two ends extending tightening the filamentary means securely thereabout by tension on the ends and securing the ends together to hold the filamentary means in the tightened position by applying a sleeve member thereover and crimping it in place.

5. The method of claim 4 wherein the tightening step comprises firstly securing the two ends of the filamentary means loosely together with a further sleeve member positioned outboard of the first and crimped in place thereover, and forcing the first sleeve apart from the further sleeve to tighten the filamentary means.

6. The method of claim 1 including the steps of wrapping the filamentary means circumferentially about a crown, and connecting the filamentary means to the stabilizing member together by means of metal bands substantially parallel to the tooth axis.

7. The method of claim 1 for removing a crown including the step of inserting between the filamentary means and the crown a plate grooved on one side to receive the filamentary means and presenting a frictional contact surface on the other side for grasping the crown, and wrapping the filamentary means circumferentially about the crown and grooved plate to thereby grasp the crown.

8. The method of claim 7 including the step of securing the filamentary means to the stabilizing member by members secured to the filamentary means on opposite sides of the crown and straddling said bolt on the stabilizing member.

9. The improved non-destructive method of removing dental caps from a tooth stub comprising the steps of wrapping filamentary means about the cap to grasp it and engaging the filamentary means by an expandible member comprising a bar with a screw therethrough positioned on the tooth stub held together with the cap to move together as a unit to thereby pull the cap from the stub as the unit moves by means of pressure on the tooth stub exerted by the screw.

10. The method of removing a crown as defined in claim 1 including the steps of placing on the circumference of the crown a plate for engaging and holding the filamentary means and contacting the filamentary means with the crown and plate about the crown circumference.

* * * * *